(12) United States Patent
Pfeil

(10) Patent No.: US 10,143,504 B2
(45) Date of Patent: Dec. 4, 2018

(54) APPARATUS AND METHOD FOR MEDIAL COMPARTMENT CORRECTION

(75) Inventor: Ingo Michael Pfeil, Langebruck (DE)

(73) Assignee: Kyon AG, Zurich (CH)

( * ) Notice: Subject to any disclaimer, the term of this patent is extended or adjusted under 35 U.S.C. 154(b) by 259 days.

(21) Appl. No.: 13/264,932

(22) PCT Filed: Apr. 18, 2010

(86) PCT No.: PCT/US2010/031531
§ 371 (c)(1),
(2), (4) Date: Jan. 30, 2012

(87) PCT Pub. No.: WO2010/121233
PCT Pub. Date: Oct. 21, 2010

(65) Prior Publication Data
US 2012/0130372 A1    May 24, 2012

Related U.S. Application Data

(60) Provisional application No. 61/170,622, filed on Apr. 18, 2009.

(51) Int. Cl.
*A61B 17/80* (2006.01)
*A61B 17/88* (2006.01)
*A61B 17/70* (2006.01)

(52) U.S. Cl.
CPC ...... *A61B 17/8061* (2013.01); *A61B 17/7059* (2013.01); *A61B 17/8004* (2013.01); *A61B 17/8095* (2013.01)

(58) Field of Classification Search
CPC ............ A61B 17/7059; A61B 17/8004; A61B 17/8061; A61B 17/8095

USPC .................................................. 606/280–299
See application file for complete search history.

(56) References Cited

U.S. PATENT DOCUMENTS

| 5,549,700 A | 8/1996 | Graham |
| 5,603,713 A * | 2/1997 | Aust et al. ............... 606/279 |
| 2005/0171544 A1 | 8/2005 | Falkner, Jr. |

FOREIGN PATENT DOCUMENTS

| DE | 43 36 932 | 5/1995 |
| EP | 0 100 114 | 2/1984 |
| EP | 0 630 624 | 12/1994 |
| EP | 0 707 838 | 4/1996 |

(Continued)

OTHER PUBLICATIONS

Goddard, A.L. (2005). "Morphology of the Canine Stance". University of Tennessee Honors Thesis Projects. http://trace.tennessee.edu/utk_chanhonoproj/855.*

(Continued)

*Primary Examiner* — Kevin T Truong
*Assistant Examiner* — Tracy Kamikawa
(74) *Attorney, Agent, or Firm* — Occhiuti & Rohlicek LLP

(57) ABSTRACT

The medial compartment is realigned by adjusting the angle of the ulna so that the head end thereof is properly aligned with the humerus. The angle of the ulna is adjusted by cutting the ulna below the head. A plate is attached to the ulna to set the new angle. The plate has two parts; one part is straight, the other is angled. Different plates have parts with different angles. A plate with a desired angle is selected to achieve the necessary angle on the ulna. The plate may be attached to the medial side or lateral side of the ulna.

8 Claims, 1 Drawing Sheet

(56) References Cited

FOREIGN PATENT DOCUMENTS

| | | |
|---|---|---|
| EP | 1 321 113 | 6/2003 |
| EP | 1 754 452 | 2/2007 |
| EP | 1754452 A1 * | 2/2007 |
| FR | 2 294 685 | 7/1976 |
| WO | WO2008/015288 | 2/2008 |
| WO | WO2008/058756 | 5/2008 |

OTHER PUBLICATIONS

Harasen, Greg "Arthrodesis—Part 1: The Carpus", Canadian Veterinary Journal, 43:641-643, 2002.

* cited by examiner

APPARATUS AND METHOD FOR MEDIAL COMPARTMENT CORRECTION

CROSS-REFERENCE TO RELATED APPLICATIONS

The present application is a U.S. national phase application, filed in accordance with 35 U.S.C: § 371, of International Application No. PCT/US2010/031531, which was filed Apr. 18, 2010, and which claims the benefit of the filing date of U.S. Provisional Application No. 61/170,622, which was filed Apr. 18, 2009. The content of these priority applications is hereby incorporated by reference herein in its entirety.

TECHNICAL FIELD (FIELD OF THE INVENTION)

The present invention relates to an apparatus and method for correcting misalignments of the medial compartment of the ulna and the humerus in the foreleg of dogs and other animals. More particularly, it relates to a device for repositioning the head end of the ulna in the foreleg of a dog or other animal in order to properly align the medial compartment with the end of the humerus.

BACKGROUND OF THE INVENTION

The present invention relates to correction of misalignments in the elbow of dogs and other animals. Arthritis of the elbow joint is the most common cause of foreleg lameness in dogs. Most of the arthritic diseases of the elbow are considered forms of dysplasia. Common causes of dysplasia include fragmented coronoid process (FCP) and medial compartment disease (MCD). In FCP, the most common form of elbow dysplasia in dogs, a fragment of bone and cartilage of the ulna is broken off. The fragment may move and cause additional damage to the joint. Furthermore, the broken bone changes the relationship between abutting surfaces of the humerus and ulna. This changed relationship causes a misalignment of the forces affecting the joint, particularly when loaded. The misaligned forces can cause cartilage damage and/or further damage to the bones.

Treatment for FCP requires removal of any bone fragments. However, this may not be sufficient if the joint has been otherwise damaged. If the joint has been severely damaged or the bones are misaligned, further damage to the joint and ongoing lameness are likely.

One method for correcting problems with the elbow joint is to replace all or part of the joint. However, elbow replacement requires extensive and complicated surgery. Despite the existence of various elbow prostheses, none has proven safe and effective for routine use.

Sliding humeral osteotomy has been proposed by Dr. Schultz at the Orthopedic Research Laboratory of the University of California. The procedure realigns the humerus to shift the forces off an area of cartilage damage. In this procedure, the humerus is cut above the elbow. A plate is used to reposition portions of the humerus bone. However, this procedure merely changes the direction of the forces. It does not adjust the angles between the humerus and the ulna nor align the interacting surfaces.

SUMMARY OF THE INVENTION

The present invention includes a procedure for realigning the humerus and ulna bones in the elbow to correct for the changed geometry of the head of the ulna from FCP or other damage to the elbow joint. The ulna is cut below the elbow. The upper part of the ulna is angled so that the head is properly aligned with the humerus. The parts of the ulna are connected together to hold them at the new angles.

According to another aspect of the invention, the elbow joint is imaged when in a loaded condition. Imaging may be done by x-ray or any other known imaging process. The image of the elbow joint is used to determine the error in alignment of the humerus and ulna bones. The necessary change in the angle of upper portion of the ulna is determined based upon the misalignment shown in the image. According to another aspect of the invention, the ulna is lengthened as part of the realignment.

According to another aspect of the invention, a plate is used to reconnect the portions of the ulna where it is cut. The plate has a flat portion and an angled portion. The upper portion of the ulna is attached to the angled portion of the plate. The lower portion of the ulna is attached to the flat portion of the plate. The plate is attached to the parts of the ulna using bone screws. According to another aspect of the invention, plates are created with angled portions at different angles. The plate used depends upon the desired adjustment in the angle of the head of the ulna.

DETAILED DESCRIPTION

Figure 1:
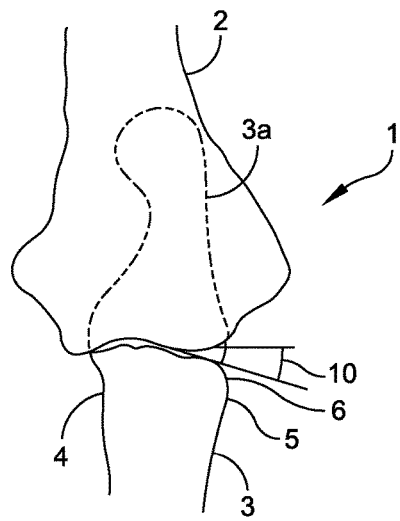
FIG. 1 is a view of the humerus and ulna in the elbow of a dog having elbow dysplasia.

FIG. 1 illustrates the problems caused by elbow dysplasia in dogs. The humerus 2 and ulna 3 bones are shown at their interaction in the elbow 1. The radius is not shown to provide a better view of the interaction between the humerus 2 and ulna 3. The elbow 1 is illustrated with the medial side 5 on the right and lateral side 4 on the left. The portion of the ulna 3a behind the humerus 2 is shown in dashed form. In a normal elbow, the humerus and ulna are aligned. When the joint is loaded, i.e., when the dog is standing, the humerus is supported evenly across the head of the ulna. However, with elbow dysplasia, as shown in FIG. 1, the bones do not interact evenly. A portion 6 of the ulna 3 is lower and does not contact the humerus 2. The lower portion of the ulna may be caused when a piece of bone is broken off, such as from FCP. It may also result from loss of cartilage. It may also be caused by poor formation of the elbow or misalignment of the bones. Regardless of the reason for the deficiency, there is a misalignment of the angle of the bones at their point of contact. The angle 10 illustrates the possible misalignment of the joint. The angle 10 represents the difference in angles between the head of the humerus 2 and the ulna 3. Typically, the misalignment occurs at the medial compartment, as illustrated in FIG. 1, but it could occur on the lateral side as well. The misalignment is most pronounced, and may only occur, when the joint is loaded. The misalignment should be visible in an x-ray of the joint. Of course, other types of imaging, such as MRI or CT scan, could be used to view the joint and any misalignment.

Figure 2:
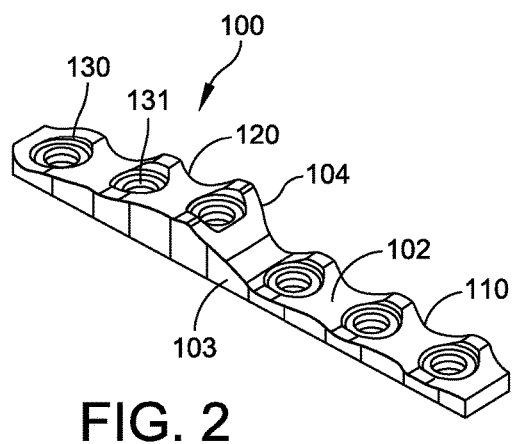
FIG. 2 is a perspective view of a plate according to an embodiment of the present invention.
Figure 3:
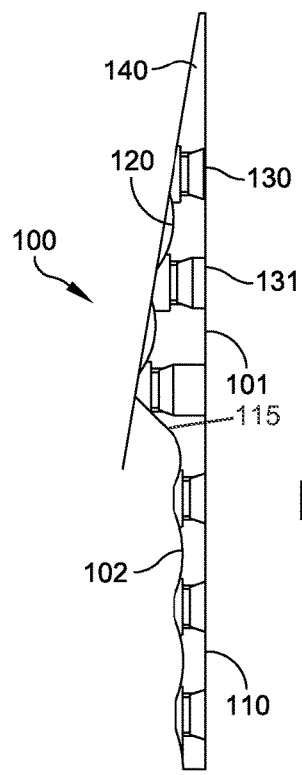
FIG. 3 is a cross sectional view of the plate of FIG. 2.

FIGS. 2 and 3 illustrate a plate 100 for use in correcting a misalignment of the humerus and ulna. The plate 100 is elongated. It is similar to other types of plates for attaching to bones. It may be of any material, but is preferably a metal. The surface may be formed or treated to allow bone ingrowth or on-growth. The plate 100 has a first side 101 and a second side 102 opposite the first side 101. The first side 101 is preferably flat. The second side 102 has a non-planar surface in order to contact the bone. The other sides 103, 104 may also be planar, or may have various other shapes. As is known with bone plates, the sides 103, 104 may be curved about screw holes 130, 131. The plate 100 has a plurality of screw holes 130, 131 for receiving bone screws to attach the plate to a bone. Preferably, the screw holes 130, 131 are recessed so that the heads of the screws are positioned below the first side 101 of the plate. Of course, other types of screw holes could be used. Any type of bone screw, including locking and non-locking screws, can be used to attach the plate 100 to the bone. Different types of screws could be used in different holes. The plate 100 in FIGS. 2 and 3 has been illustrated with six screw holes 130, 131. However, any number of screw holes could be used.

The second side 102 of the plate is shaped to create two different portions 110, 120 of the plate. In the first portion 110, the second side 102 is substantially parallel to the first side 101. In the second portion 120, the second side 102 is at an angle 140 relative to the first side 101. An angled portion 115 connects the widest part of the second portion 120 with the first portion 110. Preferably, the angled portion 115 is steep and provides a narrow transition between the portions. The angled portion may be substantially perpendicular to the first side 101.

The angle 140 of the second portion 120 of the plate 100 may be at any angle. Preferably, plates are constructed with different angles.

Figure 4:
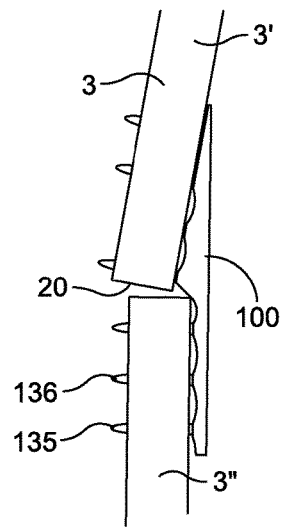
FIG. 4 is a view of a plate according to an embodiment of the invention attached to the ulna.

In order to correct the misalignment of the humerus and ulna, the image of the joint is used to determine the angle 10 (FIG. 1) of the misalignment. A plate 100 with a similar angle 140 is selected. The portion of the ulna 3 below the joint is exposed through disattachment or moving the necessary muscles and/or ligaments. As illustrated in FIG. 4, the ulna 3 is cut 20. Preferably, the cut 20 is straight across and perpendicular to the ulna 3. However, other types of cuts could be used. Preferably, the cut is not close to the head of the ulna. The distance from the head of the ulna must be sufficient to allow space for the second portion 120 of the plate 100. The plate 100 is positioned beside the ulna and attached thereto. The plate 100 may be attached to either the medial side or lateral side of the ulna, depending upon the desired adjustment to the angle. Since in most instances the medial side is lower, the plate would be positioned on the lateral side of the ulna. In attaching the plate 100, the ulna 3 may be spaced apart at the cut. Typically, the ulna has been broken or worn. This results in the ulna being shorter than the radius. The shorter ulna causes additional misalignments in the elbow. When correcting the misalignment between the ulna and the humerus, the length of the ulna can also be corrected to adjust for any difference with the radius. The plate 100 is attached to the parts 3', 3" of the ulna in the ordinary manner. Screws 135, 136 are positioned in the holes 130, 131. The plate 100 may be clamped to the parts of the bone before attachment with the screws to maintain the desired positions.

Having disclosed at least one embodiment of the present invention, various adaptations, modifications, additions, and improvements will be readily apparent to those of ordinary skill in the art. Such adaptations, modifications, additions and improvements are considered part of the invention which is only limited by the several claims attached hereto.

What is claimed is:

1. A plate for adjusting an angle of a medial or lateral compartment at the elbow, the plate comprising
    a substantially planar first side;
    a non-planar second side having a first section that is opposite to and substantially parallel to a portion of the substantially planar first side and a second section that is opposite to and angled relative to another portion of the substantially planar first side, the second section having a first free end and a second end;
    an angled portion directly connecting the first section with the second end of the second section, the angled portion generally extending along a plane transverse to the first and second sections of the non-planar second side; and
    a plurality of screw holes formed in the plate from the another portion of the substantially planar first side of the plate to the second section of the non-planar second side of the plate to attach the plate to bone,
    wherein the second section generally extends along a plane angled relative to the another portion of the substantially planar first side, the first free end and the second end of the second section lying in the plane, such that a thickness of the plate between the another portion of the substantially planar first side and the second section of the non-planar second side generally increases from the first free end of the second section to the second end of the second section where it connects to the angled portion.

2. The plate of claim 1, wherein the thickness is greater in a region centered on a given screw hole than in regions adjacent the given screw hole.

3. The plate of claim 1, wherein the angled portion connects a widest part of the second section with the first section.

4. The plate of claim 1, wherein the screw holes are recessed beneath a surface of the substantially planar first side.

5. A plurality of plates for correcting medial or lateral compartment misalignment in the elbow, wherein each plate comprises:
    a substantially planar first side;
    a non-planar second side having a first section that is opposite to and substantially parallel to a portion of the substantially planar first side and a second section that is opposite to and angled relative to another portion of the substantially planar first side, the second section having a first free end and a second end;
    an angled portion directly connecting the first section with the second end of the second section, the angled portion generally extending along a plane transverse to the first and second sections of the non-planar second side; and
    a plurality of screw holes formed in the plate from the another portion of the substantially planar first side of the plate to the second section of the non-planar second side of the plate to attach the plate to bone,
    wherein the second section generally extends along a plane angled relative to the another portion of the substantially planar first side, the first free end and the second end of the second section lying in the plane, such that a thickness of the plate between the another portion of the substantially planar first side and the second section of the non-planar second side generally increases from the first free end of the second section to the second end of the second section where it connects to the angled portion, and wherein the angle between the another portion of the substantially planar first side and the second section of the non-planar second side is different for each of the plurality of plates.

6. A method for correcting a medial or lateral compartment misalignment at the elbow, the method comprising the steps of:
cutting the ulna below the elbow; and
attaching a plate to the ulna at the cut, wherein the plate comprises
a substantially planar first side;
a non-planar second side having a first section that is opposite to and substantially parallel to a portion of the substantially planar first side and a second section that is opposite to and angled relative to another portion of the substantially planar first side, the second section having a first free end and a second end;
an angled portion directly connecting the first section with the second end of the second section, the angled portion generally extending along a plane transverse to the first and second sections of the non-planar second side; and
a plurality of screw holes formed in the plate from the another portion of the substantially planar first side of the plate to the second section of the non-planar second side of the plate to attach the plate to bone,
wherein the second section generally extends along a plane angled relative to the another portion of the substantially planar first side, the first free end and the second end of the second section lying in the plane, such that a thickness of the plate between the another portion of the substantially planar first side and the second section of the non-planar second side generally increases from the first free end of the second section to the second end of the second section where it connects to the angled portion.

7. The method of claim 6, further comprising the steps of:
creating an image of the elbow under a loaded condition;
determining an angle of misalignment of the medial or lateral compartment; and
selecting a plate to attach to the ulna from a plurality of plates having different angles between the second section and the another portion of the substantially planar first side.

8. The method of claim 6, further comprising the step of determining a length of the ulna relative to an associated radius,
wherein the step of attaching the plate includes a step of positioning the ulna so that it has a different length relative to the radius.

\* \* \* \* \*